US008815084B2

(12) United States Patent
Escrig et al.

(10) Patent No.: US 8,815,084 B2
(45) Date of Patent: Aug. 26, 2014

(54) PROCESS FOR THE TREATMENT OF SODIUM-CONTAINING HEAVY RESIDUES AND FUEL SO OBTAINED

(76) Inventors: Pilar de Frutos Escrig, Madrid (ES); Eva Maria Garcia Biosca, Madrid (ES)

( * ) Notice: Subject to any disclaimer, the term of this patent is extended or adjusted under 35 U.S.C. 154(b) by 0 days.

(21) Appl. No.: 10/977,837

(22) Filed: Oct. 29, 2004

(65) Prior Publication Data

US 2005/0234284 A1 Oct. 20, 2005

(30) Foreign Application Priority Data

Apr. 14, 2004 (EP) .................................... 04380086

(51) Int. Cl.
*C10G 17/02* (2006.01)
(52) U.S. Cl.
USPC ........................ 208/252; 208/251 R; 585/866

(58) Field of Classification Search
USPC .................................. 585/866; 208/251, 252
See application file for complete search history.

(56) References Cited

U.S. PATENT DOCUMENTS 5,210,354 A * 5/1993 Dubner et al. ................ 585/469

\* cited by examiner

*Primary Examiner* — Tam M Nguyen
(74) *Attorney, Agent, or Firm* — John C. McMahon

(57) ABSTRACT

Process for the removal of sodium from sodium-containing heavy fractions from a process for the combined production of styrene and propylene oxide comprising admixing an aqueous solution of an organic carboxylic acid to the heavy fraction at a temperature comprised between 20° C. and 100° C., and separation of the organic phase from the aqueous phase, wherein the organic phase contains less than 0.5% by weight of polymeric solids. The obtained organic phase has low viscosity and ash content and can be used directly as a fuel.

10 Claims, No Drawings

PROCESS FOR THE TREATMENT OF SODIUM-CONTAINING HEAVY RESIDUES AND FUEL SO OBTAINED

FIELD OF THE INVENTION

The present invention concerns a new process for the treatment of sodium containing heavy residues obtained for example in the production of styrene and propylene oxide and to the fuel so obtained.

DESCRIPTION OF THE PRIOR ART

A well known process for the co-production of propylene oxide and styrene monomer involves the molecular oxygen oxidation of ethyl benzene to form ethyl benzene hydroperoxide, the catalytic reaction of the hydroperoxide with propylene to form propylene oxide and 1-phenyl ethanol, and the dehydration of the 1-phenyl ethanol to styrene monomer.

In this and similar processes for the combined production of styrene and propylene oxide, a heavy oil fraction with a high sodium content is obtained as a by-product. The sodium content derives from the caustic treatment steps necessary for the process. The known propylene oxide and styrene co-production process is described, for instance, in Spanish patents nos. 314,229, 314,231, 307,877, 320,168, 323,754, 331, 818, 334,098, 335,098, 343,579 and 365,624. In a first stage, ethyl benzene is made to react at high temperature in presence of very low concentration of sodium (less than 1 ppm) with molecular oxygen in order to produce ethyl benzene hydroperoxide. The ethyl benzene hydroperoxide reacts with propylene to form propylene oxide and 1-phenyl ethanol. The mixture resulting from the epoxydation reaction is normally submitted to alkaline rinsing and to a series of distillations designed to separate the various components: propylene oxide, unreacted ethyl benzene and 1-phenyl ethanol, leaving a heavy residue with a high content of sodium and other metals.

A possible use of this heavy oil is as a low grade fuel. However, the high sodium content makes it difficult to use it because of the high solid residue after combustion.

EP 569 248 discloses a process for the reduction of sodium content by admixing to the heavy residue an aqueous acid, preferably sulphuric acid. The resulting mixture is separated into an aqueous sodium containing phase and an organic low-sodium phase. The latter is further subjected to a heat treatment before it can be used as a fuel.

EP 943 611 discloses a dehydration process of the heavy residues containing sodium and other metals, in the presence of a strong inorganic acid as a catalyst.

The above-mentioned processes have the disadvantage of producing polymerization of the unsaturated compounds as side reaction, resulting in solidification which makes it difficult to handle during the process. Additionally, when sulphuric acid is used as the acid, sulphur is introduced in the fuel with the known negative impact this can have for the environment.

Thus, there is still a need for an efficient process for the removal of sodium from sodium containing heavy fractions and production of fuel of suitable characteristics like low sulphur content and low viscosity which avoids the mentioned disadvantages.

DESCRIPTION OF THE INVENTION

It is the object of the present invention a process for the removal of sodium from sodium containing heavy fractions comprising admixing an aqueous solution of an organic carboxylic acid to the heavy fraction at a temperature comprised between 20 and 100° C., and separation of the organic phase from the aqueous phase, wherein the organic phase contains less than 0.5% by weight of polymeric solids.

In an embodiment, the sodium-containing heavy fractions are those resulting from a process for co-production of propylene and styrene monomer. In general, such a process works as follows: in a first stage, ethyl benzene is made to react at high temperature in presence of very low concentration of sodium (less than 1 ppm) with molecular oxygen in order to produce ethyl benzene hydroperoxide. The ethyl benzene hydroperoxide reacts with propylene to form propylene oxide and 1-phenyl ethanol. The mixture resulting from the epoxydation reaction is normally submitted to alkaline rinsing and to a series of distillations designed to separate the various components: propylene oxide, unreacted ethyl benzene and 1-phenyl ethanol, leaving a heavy residue with a high content of sodium and other metals.

The use of carboxylic acids is very effective in the removal of sodium and does not produce side effects like polymerisation of unsaturated compounds which solidify and make it difficult to filter the fraction. The process of the present invention results in a heavy fraction with low viscosity and easy to filter. The polymeric solid material removed by filtration is less than 0.5% by weight of the total heavy oil fraction.

The use of organic acids is also advantageous since it does not introduce sulphur in the heavy fraction. It is well known that the presence of sulphur in fuels has a negative impact on the environment, it is therefore desirable to avoid the use of sulphur in the treatment of fuels.

The obtained low-sodium heavy fraction is characterized by a low viscosity and by the absence of a relevant amount of polymeric solids (below 0.5% by weight). The absence of polymeric solid is a very important achievement in that it allows the direct use of the fuel without submitting the heavy fraction to other treatments, e.g. passage through evaporator (like in EP 569 248).

The organic carboxylic acids used according to the present invention are mono or polycarboxylic acids. Preferred monocarboxylic acids are those having between 1-8 carbon atoms or mixtures thereof. In an embodiment, the acid is selected from the list: formic acid, acetic acid, propionic acid, butyric acid, isobutyric acid, isovaleric acid, 2,2-dimetylbutyric acid, hexanoic acid, 2-methylvaleric acid, 4-methylvaleric acid, heptanoic acid, 2-methylhexanoic acid, 4-methylhexanoic acid, ethylhexanoic acid, and octanoic acid or mixtures thereof. Most preferably they are selected from the list consisting of: formic acid, acetic acid, propionic acid and ascorbic acid or mixtures thereof. In an embodiment acetic acid is preferred.

Preferred polycarboxylic acids are those having between 2-8 carbon atoms or mixtures thereof. In a particular embodiment, preferred polycarboxylic acids are those having between 3-6 carbon atoms or mixtures thereof. Preferably, the acid is selected from the list: oxalic acid, malonic acid, methylmalonic acid, succinic acid, acetoxypropionic acid, dimethylmalonic acid, ethylmalonic acid, glutaric acid, oxalacetic acid, methyl succinic acid, adipic acid, ascorbic acid, isoascorbic acid, acetonedicarboxylic acid and 2-ketoglutaric acid. Most preferably, they can are selected from the list consisting of tartaric acid, adipic acid and citric acid or mixtures thereof.

The aqueous solution of the carboxylic acid can vary in a large range of concentration. However, it is preferred to use a solution wherein concentration of the acid is from 2% to 20% by weight.

The concentration of the solution also depends on the ratio water phase/organic phase. At higher ratios it is in fact possible that the water phase becomes lighter than the organic phase, and this is sometimes preferable. Thus, when operating with water as the upper phase, the concentration of acid is preferably comprised between 2% and 5% by weight, when operating with the organic phase as the upper phase, the preferred concentration of acid is between 6% and 20% by weight.

The carboxylic acid is used in an amount that is normally at least stoichiometric with respect to sodium.

The temperature of the treatment can vary in a broad range and is generally comprised between 20° C. and 100° C., preferably 50° C. to 100° C. When water is the upper phase, the most preferred temperature is comprised between 50° C. and 70° C. When the organic phase is the upper phase, the most preferred temperature is comprised between 70° C. and 90° C.

The heavy fraction and the aqueous solution of the carboxylic acid are intensively mixed for a period of time preferably comprised between a few seconds and a few hours, depending on the mixing device. Normally, a contact time comprised between 1 and 30 minutes is enough to obtain an effective removal of sodium. The mixing can be performed by using any industrial mixer, e.g. a static mixer or a stirred tank. After contact with the carboxylic acid, the water and the organic phase are separated, according to methods well known in the art, e.g. using a decanter or a centrifuge.

The organic phase obtained after treatment with the carboxylic acid is characterized not only by a very low level of solids, but also by a low amount of ash and by a low viscosity.

Preferably the amount of ash is lower than 0.4% w/w, most preferably below 0.25% w/w.

The viscosity at 50° C. of the organic phase after treatment is preferably below 210 centistokes, most preferably below 100 centistokes.

In one aspect of the invention it is advantageous that the viscosity at 50° C. of the organic phase be below 100 centistokes. In this case the carboxylic acid used is not oxalic acid. This makes the resulting fuel easier to handle and improves its properties. Thus, in an embodiment of the invention the acid is not oxalic acid.

The invention is further illustrated by way of examples.

EXAMPLES

The fuel, after and before the treatment was characterized using the following methods: the sodium content was measured using a flame photometer after dilution of the fuel in ethanol, all the sodium contents was expresed in percent weight/weight. The cinematic viscosity was measured using the adecuated viscosimeter immersed in a 50° C. oil bath and is expressed in centistokes (csk). The ash content was determined by means of calcination at 800° C. during four hours and is expressed in percent weight/weight (wt/wt). We checked the possible formation of polymer solid by filtration of the mixture at 80° C. using a 0.45 micron poro size filter.

Comparative Example 1

A sodium rich heavy fraction obtained from the styrene-propylene oxide process (0.95% by weight Na) was characterized obtaining an ash content (solid residue after calcination at 800° C.) of 1.35% w/w and a viscosity of 238 csk, at 50° C. The procedure of the treatment was the following: the heavy fraction (100 g) was heated until a temperature of 80° C. and a solution of sulfuric acid in water (25 g, 8% w/w) was added and mixed at 80° C. during fifteen minutes. Then, the mixture was centrifuged at 4.500 rpm during five minutes and the two phases (organic and aqueous) were separated. The organic phase was separated in the upper fraction and was characterized obtaining a value of ashes of 0.3% w/w and a viscosity value of 60 csk at 50° C. In this case it was observed the presence of a polymeric solid phase at the bottom of the centrifuge tube, well above 1%. The solid made it impossible to filter the residue unless the residue itself was heated at a temperature above 100° C.

Example 2

Example 1 was repeated using a solution of oxalic acid (25 g, 10.5% w/w). The organic phase was separated in the upper fraction. The ash content of the final organic phase was 0.16% w/w and the viscosity at 50° C. of the final organic phase was 142 csk. We checked the possible formation of polymer solid by filtration of the mixture at 80° C., the mixture was filtered without problems and the quantity of the solid retained in the filter was less than 0.5% w/w.

Example 2A

Example 2 was repeated using 12.5 g of a more concentrated oxalic acid (21% w/w). The organic phase was separated in the upper fraction. The ash content of the final organic phase was 0.2% and the viscosity at 50° C. of the final organic phase was 184 csk the mixture was filtered without problems and the quantity of the solid retained in the filter was less than 0.5% w/w.

Example 2B

Example 2 was repeated using 100 g of a more diluted oxalic acid (2.6% w/w) heating the mixture at 60° C. The organic phase was separated in the heavy fraction, the ash content of the final organic phase was 0.15% and the viscosity at 50° C. of the final organic phase was 205 csk the mixture was filtered without problems and the quantity of the solid retained in the filter was less than 0.5% w/w

Example 2C

Example 2 was repeated using a mixing temperature of 25° C. The organic phase was separated in the upper fraction. The ash content of the final organic phase was 0.6% and the viscosity at 50° C. of the final phase was 190 csk. The mixture was filtered without problems and the quantity of the solid retained in the filter was less than 0.5% w/w.

Example 2D

Example 2 was repeated using a mixing temperature of 60° C. The organic phase was separated in the upper fraction. The ash content of the final organic phase was 0.4% and the viscosity at 50° C. of the final phase was 193 csk. The mixture was filtered without problems and the quantity of the solid retained in the filter was less than 0.5% w/w.

Example 3

Example 1 was repeated using a solution of formic acid (25 g, 7.5% w/w). The organic phase was separated in the upper fraction. The ash content of the final organic phase was 0.41% w/w and the viscosity at 50° C. of the final organic phase was 65 csk. The mixture was filtered without problems and the quantity of the solid retained in the filter was less than 0.5% w/w.

Example 4

Example 1 was repeated using a solution of adipic acid (25 g, 12% w/w). The organic phase was separated in the upper fraction. The ash content of the final organic phase was 0.17% w/w and the viscosity at 50° C. of the final organic phase was 70 csk. The mixture was filtered without problems and the quantity of the solid retained in the filter was less than 0.5% w/w.

Example 5

Example 1 was repeated using a solution of tartaric acid (25 g, 12.5% w/w). The organic phase was separated in the upper fraction. The ash content of the final organic phase was 0.69% w/w and the viscosity at 50° C. of the final organic phase was 69 csk. The mixture was filtered without problems and the quantity of the solid retained in the filter was less than 0.5% w/w.

Example 6

Example 1 was repeated using a solution of acetic acid (25 g, 10% w/w). The organic phase was separated in the upper fraction. The ash content of the final organic phase was 0.20% w/w and the viscosity at 50° C. of the final organic phase was 33 csk the mixture was filtered without problems and the quantity of the solid retained in the filter was less than 0.5% w/w.

Example 7

Example 1 was repeated using a solution of citric acid (25 g, 11.5% w/w). The organic phase was separated in the upper fraction. The ash content of the final organic phase was 0.06% w/w and the viscosity at 50° C. of the final organic phase was 97 csk. The mixture as filtered without problems and the quantity of the solid retained in the filter was less than 0.5% w/w.

Example 8

Example 1 was repeated using a solution of ascorbic acid (25 g, 14.5% w/w). The organic phase was separated in the upper fraction. The ash content of the final organic phase was 0.28% w/w and the viscosity at 50° C. of the final organic phase was 73 csk. The mixture was filtered without problems and the quantity of the solid retained in the filter was less than 0.5% w/w.

The invention claimed is:

1. A process for the removal of sodium from sodium-containing heavy fraction, resulting from combined production of styrene and propylene oxide, the process comprising:
admixing an aqueous solution of from 2% to 20% by weight of an acid selected from the group consisting of monocarboxilic acids having between 1 and 8 carbon atoms, polycarboxilic acids having between 3 and 8 carbon atoms and mixtures thereof, to the heavy fraction at a temperature in the range between 20 and 100° C., and
separating an organic phase from an aqueous phase without any intermediate process of purification such that the organic phase is free of sodium and the aqueous phase contains all of the sodium, so as to thereby obtain a modified organic phase that is thereafter usable as a fuel and that contains less than 0.5% by weight of polymeric solids and further that has a viscosity below 100 centistokes at 50° C.

2. The process according to claim 1, wherein the acid is selected from a group consisting of monocarboxylic acids having between 1 and 8 carbon atoms and mixtures thereof.

3. The process according to claim 2, wherein the acid is selected from the group consisting of: formic acid, acetic acid, propionic acid, ascorbic acid and mixtures thereof.

4. The process according to claim 1, wherein the acid is selected from the group consisting of: tartaric acid, adipic acid, citric acid and mixtures thereof.

5. The process according to claim 1, wherein after mixing, the aqueous phase is an upper phase and the concentration of acid in the aqueous phase is in the range between 2 and 5% by weight.

6. The process according to claim 1, wherein after mixing, the organic phase is an upper phase and the concentration of acid in the aqueous phase is in the range between 6 and 20% by weight.

7. The process according to claim 1, wherein after mixing, the organic phase is an upper phase and the temperature is in the range between 70° C. and 90° C.

8. The process according to claim 1 wherein the polycarboxylic acid has between 3 and 6 carbon atoms.

9. A process for the removal of sodium a from sodium-containing heavy fraction, resulting from combined production of styrene and propylene oxide, the process comprising:
admixing an aqueous solution of an acid selected from the group consisting of monocarboxilic acids having between 3 and 8 carbon atoms, polycarboxilic acids having between 3 and 8 carbon atoms and mixtures thereof, to the heavy fraction at a temperature in the range between 20 and 100° C., and
separating an organic phase containing no sodium from an aqueous phase containing all of the sodium without any intermediate process of purification so as to obtain a modified organic phase that is thereafter usable used as a fuel and that contains less than 0.5% by weight of polymeric solids and further that has a viscosity below 100 centistokes at 50° C.

10. A process for the removal of sodium from sodium-containing heavy fraction, resulting from combined production of styrene and propylene oxide, the process consisting of:
a) admixing an aqueous solution of from 2% to 20% by weight of an acid selected from the group consisting of monocarboxilic acids having between 1 and 8 carbon atoms, polycarboxilic acids having between 3 and 8 carbon atoms and mixtures thereof, to the heavy fraction at a temperature in the range between 20 and 100° C., and
b) separating an organic phase from an aqueous phase without any intermediate process of purification such that the organic phase is free of sodium and the aqueous phase contains all of the sodium, so as to thereby obtain a modified organic phase that is thereafter usable as a fuel and that contains less than 0.5% by weight of polymeric solids and further that has a viscosity below 100 centistokes at 50° C.

* * * * *